(12) United States Patent
Shurgalin et al.

(10) Patent No.: US 10,206,744 B2
(45) Date of Patent: Feb. 19, 2019

(54) WAVEGUIDE LOCKS AND COUNTERBALANCES FOR WAVEGUIDE CONDUITS

(71) Applicant: OmniGuide, Inc., Lexington, MA (US)

(72) Inventors: Max Shurgalin, Bedford, MA (US); Marc Graham, Somerville, MA (US)

(73) Assignee: OmniGuide, Inc., Lexington, MA (US)

( * ) Notice: Subject to any disclaimer, the term of this patent is extended or adjusted under 35 U.S.C. 154(b) by 0 days.

(21) Appl. No.: 15/973,362

(22) Filed: May 7, 2018

(65) Prior Publication Data

US 2018/0256255 A1 Sep. 13, 2018

Related U.S. Application Data

(63) Continuation of application No. 14/210,748, filed on Mar. 14, 2014, now Pat. No. 9,980,775.

(60) Provisional application No. 61/789,472, filed on Mar. 15, 2013.

(51) Int. Cl.
| | | |
|---|---|---|
| A61B 18/18 | (2006.01) | |
| A61B 18/22 | (2006.01) | |
| A61B 17/00 | (2006.01) | |
| A61B 18/20 | (2006.01) | |

(52) U.S. Cl.
CPC .... *A61B 18/22* (2013.01); *A61B 2017/00526* (2013.01); *A61B 2018/202* (2013.01); *A61B 2018/225* (2013.01); *Y10T 29/49826* (2015.01)

(58) Field of Classification Search
CPC .......................... A61B 18/22; A61B 2018/225
USPC ................. 606/1, 2, 13, 16; 607/88–90, 93
See application file for complete search history.

(56) References Cited

U.S. PATENT DOCUMENTS

| | | |
|---|---|---|
| 4,652,083 A | 3/1987 | Laakmann |
| 4,688,893 A | 8/1987 | Laakmann |
| 4,760,840 A | 8/1988 | Fournier et al. |
| 4,881,524 A | 11/1989 | Boebel et al. |
| 5,047,049 A | 9/1991 | Salai |
| 5,440,664 A | 8/1995 | Harrington et al. |
| 5,567,471 A | 10/1996 | Harrington et al. |
| 5,951,544 A | 9/1999 | Konwitz |
| 6,463,200 B2 | 10/2002 | Fink et al. |
| 6,788,864 B2 | 9/2004 | Ahmad et al. |
| 6,801,698 B2 | 10/2004 | King et al. |
| 6,898,359 B2 | 5/2005 | Soljacic et al. |

(Continued)

FOREIGN PATENT DOCUMENTS

| | | |
|---|---|---|
| WO | 2010/053575 A2 | 5/2010 |
| WO | 2014/043697 A2 | 3/2014 |

OTHER PUBLICATIONS

Extended European Search Report, dated Oct. 31, 2016, for European Application No. 14763838.1-1666, 8 pages.

(Continued)

*Primary Examiner* — John R Downey
(74) *Attorney, Agent, or Firm* — Seed Intellectual Property Law Group LLP (57) ABSTRACT

An optical radiation delivery structure including a waveguide conduit having a surgical access portion and a handle portion. The handle portion includes a gripping portion and a waveguide lock, which is configured to have only a locked state and an unlocked state. In some embodiments, the handle portion includes a gripping portion and a counterbalance region, such that a center of mass of the waveguide conduit is disposed towards a proximal end of the waveguide conduit.

19 Claims, 10 Drawing Sheets

(56) References Cited

U.S. PATENT DOCUMENTS

| | | |
|---|---|---|
| 7,142,756 B2 | 11/2006 | Anderson et al. |
| 7,226,444 B1 | 6/2007 | Ellman et al. |
| 7,272,285 B2 | 9/2007 | Benoit et al. |
| 7,295,734 B2 | 11/2007 | Bayindir et al. |
| 7,311,962 B2 | 12/2007 | Fink et al. |
| 7,315,675 B2 | 1/2008 | Harrington et al. |
| 7,331,954 B2 | 2/2008 | Temelkuran et al. |
| 8,414,196 B2 | 4/2013 | Lu et al. |
| 8,517,933 B2 | 8/2013 | Mohr |
| 2002/0186934 A1 | 12/2002 | Hug et al. |
| 2003/0195559 A1 | 10/2003 | Colgan et al. |
| 2005/0259934 A1 | 11/2005 | Temelkuran et al. |
| 2009/0060418 A1 | 3/2009 | Munn |
| 2009/0171372 A1 | 7/2009 | Mohr |
| 2009/0248041 A1 | 10/2009 | Williams et al. |
| 2009/0299352 A1 | 12/2009 | Zerfas et al. |
| 2010/0216088 A1 | 8/2010 | Bierbaum et al. |
| 2010/0249507 A1 | 9/2010 | Prisco et al. |
| 2010/0292681 A1 | 11/2010 | Fortuna et al. |
| 2011/0004203 A1 | 1/2011 | Zipper |
| 2013/0064515 A1 | 3/2013 | Shurgalin et al. |

OTHER PUBLICATIONS

International Search Report and Written Opinion, dated Sep. 11, 2014, for International Application No. PCT/US2014/027754, 7 pages.

WAVEGUIDE LOCKS AND COUNTERBALANCES FOR WAVEGUIDE CONDUITS

TECHNICAL FIELD

This invention relates to handpieces and other conduits for optical radiation waveguides and more particularly to locks and counterbalances for waveguide conduits.

BACKGROUND

There is a trend toward less invasive surgical procedures performed by introducing small diameter, flexible tools into natural body openings and small incisions. These tools can enable tissue visualization, imaging, analysis, manipulation, cutting, coagulation, and removal. An example of a procedure done through a natural body opening is polyp visualization and removal during a colonoscopy. Examples of procedures done through one or more small incisions include laparoscopic hysterectomy or cholecystectomy. Laparoscopic incisions are typically 3 mm to 15 mm in diameter. Some procedures can be done through incisions 3 mm or smaller, and have been called "needlescopic". One type of laparoscopic surgery is single incision laparoscopic surgery, where a multiport trocar is used to introduce a cluster of surgical tools. Incisions that start from an instrument already in a natural body opening, called natural orifice translumenal endoscopic surgery ("NOTES"), are a topic of current surgical research, as are various percutaneous procedures. Examples include NOTES cholecystectomy.

A small-diameter, flexible tool can be beneficial for such procedures. To access regions that are not necessarily close to the point of tool introduction, longer tools may also be desirable.

Long, thin, flexible waveguides for optical radiation are well adapted for performing the procedures described above, and suit the current growing interest in and use of laser surgery. For example, solid core silica fibers are used to guide wavelength of KPT (532 nm), Nd:YAG (1.06 µm), Ho:YAG (2.1 µm) and Tm:YAG (2 µm) lasers widely used in medical applications. For $CO_2$ laser beams (approximately 10.6 µm wavelength), hollow waveguides may be useful, as the $CO_2$ wavelength is generally highly absorbed in materials traditionally used for optical fibers, such as silicates and thermoplastic polymers. Hollow waveguides may be made of metal, such as disclosed in U.S. Pat. Nos. 4,652,083 and 4,688,893, or metalized tubes such as disclosed in U.S. Pat. Nos. 5,440,664; 5,567,471; and 7,315,675 to Harrington et al., in which a metal mirror guides the optical radiation.

Flexible hollow waveguides are manufactured in some techniques by drawing structured thermoplastic preforms. Examples of such a structure are described by Fink et al. in U.S. Pat. Nos. 6,463,200 and 7,311,962 in which a dielectric stack of materials having different refractive indices is arranged in concentric cylinders about the waveguide axis thus providing the mirror structure that guides the radiation. Flexible hollow waveguides drawn from structured thermoplastic preforms are also disclosed in U.S. Pat. No. 7,272,285 to Benoit et al. and U.S. Pat. No. 7,295,734 to Bayindir et al., as well as in the following U.S. Patents assigned to OmniGuide, Inc.: U.S. Pat. No. 6,788,864 by Ahmad et al.; U.S. Pat. No. 6,801,698 by King et al.; U.S. Pat. No. 6,898,359 by Soljacic et al.; and U.S. Pat. No. 7,142,756 by Anderson et al.

Generally, waveguides may be strengthened and protected by additional elements on the outside, such as jackets, and may have additional elements that add functionality, such as distal tips. Waveguides disposed inside protective jackets and having additional functionality elements are often referred to as waveguide assemblies.

For further mechanical strength and manipulation, it is often desirable to place waveguides or waveguide assemblies inside other mechanical structures, known as waveguide conduits, which may provide protection, strength, and structure for surgical access control. Waveguide conduits are typically placed on or over waveguides or waveguide assemblies after manufacturing or assembly of the waveguides, generally at point of use. Waveguide conduits can be either flexible or rigid, or have a rigid portion and a flexible portion. A waveguide conduit can have multiple functions. A primary and important function of the waveguide conduits is to give a user control of surgical access, in either a hand-held manner, known as handpiece-style waveguide conduits, or by means of electromechanical actuators or robotic devices such as Flexguide™ products available from OmniGuide, Inc., based in Cambridge, Mass.

Examples of known robotic surgical systems utilizing lasers and other instruments are provided by Mohr in U.S. Patent Publication No. 2009/0171372, by Williams et al. in U.S. Patent Publication No. 2009/0248041 and by Prisco et al. in U.S. Patent Publication No. 2010/0249507, for example, all assigned to Intuitive Surgical Operations, Inc. and/or Intuitive Surgical, Inc. of Sunnyvale, Calif., which provides the Da Vinci™ robotic platform. Robotically assisted surgery through a single port utilizing an image capturing device and multiple surgical tools is described by Mohr in U.S. Pat. No. 8,517,933.

Other functional elements may include mechanical protection of the waveguide, control of waveguide bending for surgical access and control of associated optical performance variation (optical loss due to bends) of the waveguide, means for keeping the waveguide inside the waveguide conduit and optically aligned with the conduit distal tips during usage, couplers for mechanical coupling of the waveguide conduit with an external manipulator, and mechanical supports of other functional elements that may be affixed to the conduit (e.g., distal tips, suction and/or irrigation tools, etc.). The waveguide conduit is preferably steerable in a well-controlled and precise motion manner, critical for minimally invasive surgical procedures, by means of a handle and/or attachment to a manipulator. It is preferably sterilizable and may be disposable or reusable.

Suitable materials for the waveguide conduit portions include stainless steel (e.g., 300 and 400 series surgical grade steels), titanium, aluminum, various alloys of aluminum, ceramic materials such as alumina and zirconia, and polymer materials such as silicones, polyamides, polycarbonates, PEEK, and polyolefin.

The configuration of the waveguide conduit depends on the particular application. It may vary in length and may contain several bends placed anywhere between distal (adjacent to the surgical site) and proximal ends (closer to the surgeon or other user of the device), depending on the requirements of a particular application. For example, conduits used for oral surgeries (e.g., base of tongue), are generally rigid and relatively short with fewer bends than waveguide conduits used for laryngeal work. A typical range of bend angles between distal and proximal ends is 20°-60° and total length may be from about 5 cm to about 25 cm for oral surgeries, while for laryngeal surgical procedures the bend angles maybe larger, up to 90°, and the total length may be up to about 45 cm. Yet for laparoscopic procedures, even longer waveguide conduits are utilized, up to about 65 cm.

Giving a surgeon precise control of waveguide position and direction of firing laser radiation is important. Therefore, waveguide conduits for handheld usage generally have handles designed for a comfortable grip, for example, as in OmniGuide ENT handpieces, sold in ENT handpiece sets, catalog number ENT-HS. However, the longer waveguide conduits can present an issue with tremor from a user's hand or other source of vibration being amplified at the distal end. In addition, over longer periods of use in a hand-held manner, hand and finger fatigue may develop and result in decreasing ability for precision manipulation and aiming due to surgeon hand fatigue.

Figure 1:
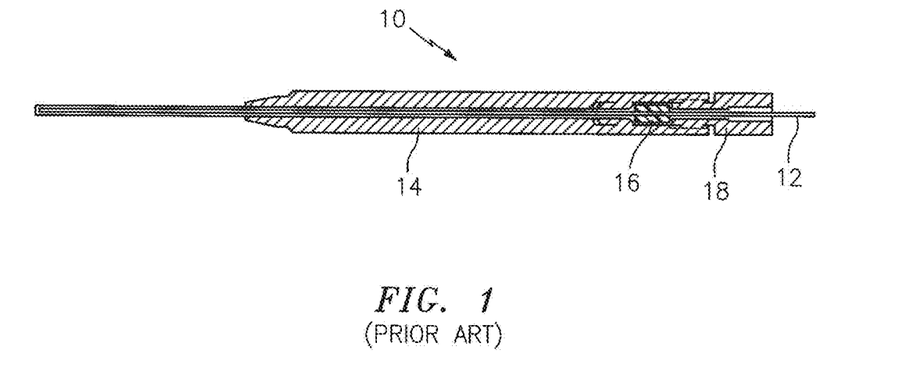
FIG. 1 is a schematic cross-sectional view of a waveguide disposed into a prior art handpiece-type conduit with a threaded cap and compression gripper.

Some approaches to fix waveguides in place are known to those skilled in the art. For example, one prior art laser radiation delivery structure 10, FIG. 1, releasably secures a single-use waveguide 12 inserted through a reusable rigid waveguide conduit 14, also referred to as a handpiece 14, of the delivery structure 10. An elastic compression gripper 16 and a threaded cap 18 are included in the proximal portion of the handpiece 14. When the cap 18 is rotated, it acts on the gripper 16 and compresses it onto the waveguide 12 when rotated in a first angular direction and allows the gripper 16 to relax and release the waveguide 12 when rotated in the opposite angular direction. This method to keep waveguides in place is used, for example, in Omni-Guide handpieces, sold in handpiece sets, catalog number ENT-HS. While using a soft elastic gripper may reduce potential for mechanical degradation of the waveguide, a disadvantage of such a method may be variable control of the gripping force and compression exerted on the waveguide, due to variation in the gripper material properties and gripper dimensions, which can be challenging to control to tight tolerances due to the elastic nature of the material. Also, the gripper may wear over time and variability in the waveguide diameter and the user action of tightening the cap can affect the reliability of the grip on the waveguide.

It is desirable to have a waveguide conduit which enables a surgeon to exercise precise control and aiming of laser radiation delivered via a waveguide with minimal amount of tremor and minimal hand fatigue over time.

It is desirable to reliably keep a waveguide in a waveguide conduit and to hold a waveguide properly during use and manipulation, thus avoiding excessive protrusion or recess of the waveguide distal end relative to a distal tip of the waveguide conduit, as well as minimizing uncontrolled changes in the waveguide position.

BRIEF SUMMARY

An object of the present invention is to enable rapid and easy engagement and disengagement of a waveguide relative to a waveguide conduit.

Another object of the present invention is to enhance the ergonomic feel and control during use of a handpiece for a waveguide.

This invention features an optical radiation delivery structure with a waveguide conduit including a surgical access portion and a handle portion, the handle portion having a gripping portion graspable by a user. The structure further includes a waveguide lock configured to have only (i) a locked state during which a waveguide inserted into the waveguide conduit is fixedly held and (ii) an unlocked state during which the waveguide is freely slidable relative to the waveguide conduit.

In some embodiments, the waveguide lock is biased to be in the locked state, and the waveguide lock includes (a) a clamp that is movable transversely to the waveguide and (b) a spring element that biases the clamp against the waveguide. In certain embodiments, (i) the handle portion includes a waveguide lock housing having a first inner surface, (ii) the waveguide lock is disposed in the waveguide lock housing, (iii) the waveguide lock includes a collet structure having a first outer surface, and (iv) at least one of the first inner surface of the housing and the first outer surface of the collet structure being tapered to (a) enable the collet structure to move radially outwardly when the waveguide lock is moved from the locked state to the unlocked state and (b) force the collet structure against the waveguide in the locked state. Preferably, the collet structure includes at least two jaws and at least two cantilevered arms, each jaw being disposed on a distal end of a cantilevered arm.

In a number of embodiments, the waveguide lock includes one of a release button, a push button and a slide button. In some embodiments, the handle portion includes a counterbalance region such that a center of mass of the waveguide conduit is closer to a proximal end of the waveguide conduit. In one embodiment, a largest cross-sectional dimension of the counterbalance region is at least as large as a largest cross-sectional dimension of the gripping portion of the handle. In an embodiment, the counterbalance portion is cylindrical and the gripping portion has at least one flat portion.

In some embodiments, the surgical access portion includes a cannula having a distal tip disposed on the cannula, and the waveguide is insertable through the waveguide conduit until the waveguide reaches the distal tip of the cannula. In one embodiment, the waveguide lock housing defines at least one opening for cleaning and sterilization.

This invention also features a laser radiation delivery structure including a waveguide conduit having a surgical access portion and a handle portion with a gripping portion and a counterbalance region, such that a center of mass of the waveguide conduit is disposed towards a proximal end of the waveguide conduit.

This invention further features a method of securing a waveguide within a laser radiation delivery structure, including selecting a waveguide conduit with a surgical access portion and a handle portion, the handle portion having a gripping portion and a waveguide lock, wherein the waveguide lock is configured to have only a locked state and an unlocked state. The method further includes inserting a waveguide into the waveguide conduit while placing the waveguide lock in the unlocked state, such as by imparting a linear motion to the waveguide lock, and placing the waveguide lock in the locked state to fixedly hold the waveguide in a selected axial position relative to the waveguide conduit.

BRIEF DESCRIPTION OF THE DRAWINGS

In what follows, preferred embodiments of the invention are explained in more detail with reference to the drawings, in which.

DETAILED DESCRIPTION

This invention may be accomplished by a structure for locking repeatably and reliably a waveguide or waveguide assembly in a waveguide conduit that may be used with waveguides of varying outside diameter and texture, and enable user-independent waveguide retention without axial migration or mobility, preferably without rotational mobility, and most importantly without affecting waveguide optical performance and reliability. Embodiments of the invention prevent inadvertent release of the waveguide and at the same time allow easy release of the waveguide when needed. Embodiments of the invention also allow easy cleaning and sterilization after use of the waveguide conduit. Preferably, a counterbalance portion is included to increase control and precision of surgical access during use and manipulation.

For applications in minimally invasive laser surgery, in which laser radiation is delivered by a flexible waveguide, it is desirable to have the waveguide disposed in a waveguide conduit that includes a surgical access portion and a handle portion. The handle portion includes a gripping portion, graspable by a user, and a waveguide lock for reliable fixing of waveguide position in the waveguide conduit during use and manipulation, substantially preventing axial and preferably rotational motion of the waveguide inside the waveguide conduit. At the same time, the waveguide lock preferably minimizes any degradation of optical performance of the locked waveguide that may result in inferior performance and reliability. Therefore the forces the waveguide lock may exert on the waveguide are limited by the waveguide opto-mechanical characteristics, yet the retention of the waveguide is preferably maintained at levels that enable proper use and operation of the laser radiation delivery system.

A waveguide lock according to the present invention is configured to have only two states, that is, locked and unlocked. The unlocked state can be configured to require continuous actuation by a user, such as a linearly-applied pressure, because the lock is biased toward the locked state. The surgical access portion may include a cannula portion configured to reach to the surgical site in a minimally invasive manner, and a distal portion, which may be either (i) an opening of the cannula portion at the distal end aligned with the waveguide distal end, and thus enabling emission of the laser radiation out of the waveguide, or (ii) a distal tip with additional features and functionality.

Figure 2:
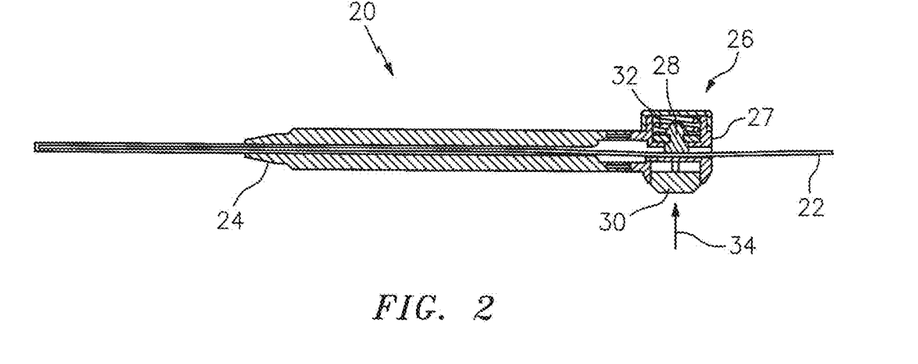
FIG. 2 is a schematic cross-sectional view of a waveguide fixed inside a waveguide conduit by a spring-loaded clamp mechanism, in accordance with an embodiment of the present invention.

An optical radiation delivery structure 20 according to the present invention, FIG. 2, includes a rigid conduit 24 and a waveguide lock assembly 26 for releasably holding a single-use optical waveguide 22 (or a waveguide assembly, such as a waveguide disposed in a jacket, all hereinafter "waveguide") which is releasably fixed inside the reusable waveguide conduit 24 by the lock assembly 26a. In this construction, lock assembly 26 is a spring-loaded clamp mechanism, in which the waveguide 22 is releasably held in a fixed position in a lock housing 27 by a clamp 28 moved, in this construction, radially outwardly by a control mechanism such as push button 30, which the user presses in a linear, radially inwardly release direction indicated by arrow 34 to overcome the inward biasing force of spring 32. When button 30 is fully depressed to rest against a stop or against the floor of the cavity in which the button moves in a linear fashion, the waveguide 22 is fully released relative to delivery structure 20.

The surface of clamp 28 which contacts waveguide 22 is flat in one construction and, in another construction, has a groove or channel with a "U-" or "V-" shaped cross-section. The clamp portions contacting the waveguide 22 are formed of a rigid material in some constructions and, in other constructions, have an elastic, resilient and/or friction-enhancing padding to reduce concentrated compression forces on the waveguide and at the same time to increase the contact surface area. Activation and spring force direction is substantially radial or perpendicular to a longitudinal axis of the waveguide in this construction.

Figure 3:
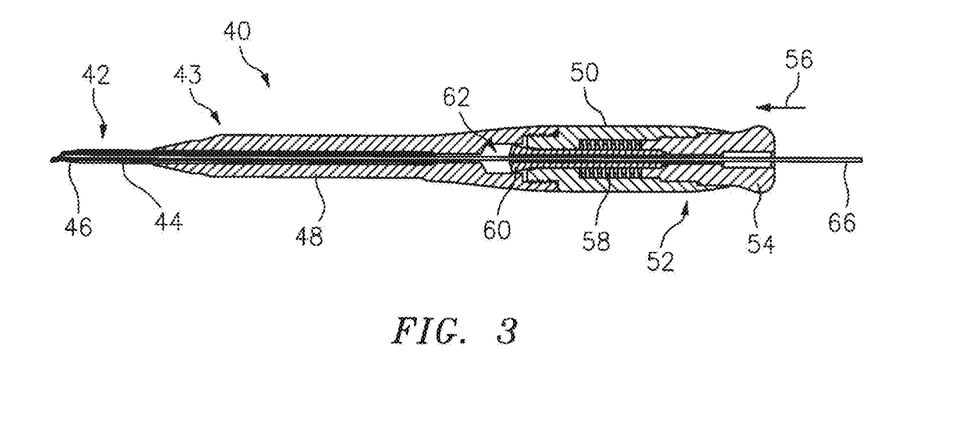
FIG. 3 is a schematic cross-sectional view of a waveguide conduit that includes a surgical access portion and a handle portion, with a collet-type biased lock in accordance with an embodiment of the invention.

Laser radiation delivery structure 40, FIG. 3, includes a surgical access portion 42 and a handle portion 43. The surgical access portion 42 includes a cannula 44 terminating in a distal tip 46. In one construction, distal tip 46 includes a stop to restrict distal advancement of a waveguide and, in another construction, distal tip 46 has a wholly open orifice. Several possible distal tip configurations are disclosed in U.S. Pat. No. 7,331,954 by Temelkuran et al. and in US Patent Publication No. 2013/0064515 by Shurgalin et al., for example. The handle portion 43 has a gripping portion 48 and a counterbalance portion 50, described in more detail below, that includes a collet-type locking mechanism 52 in this construction. The waveguide lock 52 is configured to have only two states, i.e., locked and unlocked. The waveguide lock 52 is disengaged by a push button mechanism 54, which is pressed by a user in a distal, axial direction indicated by arrow 56, which overcomes a proximal, axial biasing locking force generated by compression spring 58 to move jaws of collet structure 60 into a chamber 62 defined within handle 48. The outer surfaces of the collet jaws are thereby slid away from inner bearing surface 64 of portion 50 so that the jaws release their radially-inwardly-directed clamping grip on a single-use waveguide 66.

During initial set-up, push button 54 is depressed in the distal direction of arrow 56 and the waveguide 66 is advanced distally until it reaches a desired location within cannula 44, preferably substantially at distal tip 46. The user then releases button 54, and spring 58 automatically forces collet structure 60 in a proximal direction to engage collar-like bearing surfaces 64 to force the jaws of collet structure 60 against the outer surface of waveguide 66 to secure it in the desired axial position relative to delivery structure 40.

Typical cannulas suitable for use as surgical access portion 42 are well known to those skilled in the art, e.g., cannulas made of cylindrical stainless steel tubing with internal diameters ranging from 0.018" to 0.071" and external diameters ranging from 0.039" to 0.095" and contain one or two bends for surgical access, for example, cannulas found in OmniGuide ENT handpieces, sold in ENT handpiece sets, catalog number ENT-HS. For example, Flexguide™ products available from OmniGuide, Inc., based in Cambridge, Mass., have a distal tip disposed at the end of the cannula conduit.

Figure 4:
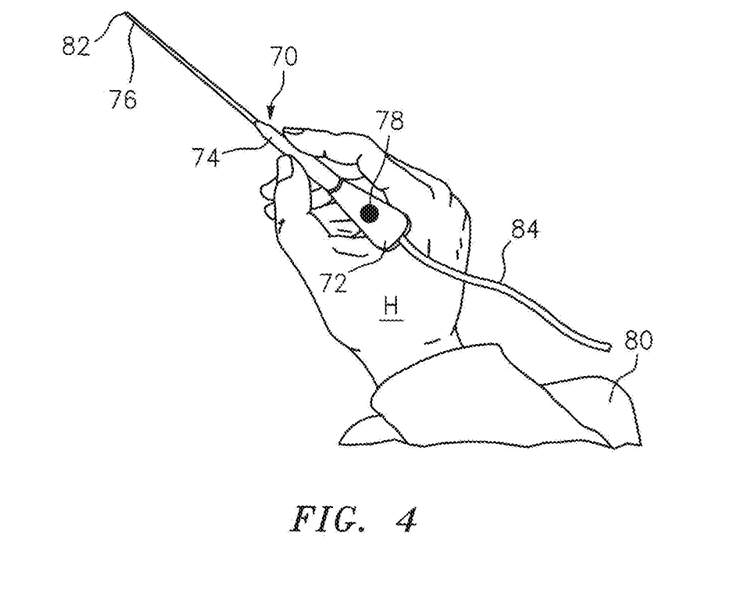
FIG. 4 is a schematic perspective view of a waveguide conduit being held by a surgeon's hand, in accordance with an embodiment of the invention.

Mass and mass distribution over the length of the waveguide conduit is advantageously configured according to the present invention to provide a counterbalance that may be helpful during surgery. Referring to FIG. 4, a user's hand H, e.g., a surgeon's hand, holds and manipulates a waveguide conduit 70 during use in a surgical procedure. Waveguide conduit 70 includes a proximal counterbalance portion 72, a handle gripping portion 74 and a distal cannula portion 76. In this construction, counterbalance portion 72 rests on the surgeon's hand, because of added weight provided by the counterbalance portion 72 shifts the location of center of mass 78 to the location shown in FIG. 4. Preferably, the surgeon's arm receives support from a hand-rest, a wrist-rest or an arm-rest 80 typically employed for longer duration surgical procedures. The counterbalance portion 72 shifts the center of mass of the whole waveguide conduit to the point where the waveguide conduit rests on the surgeon's hand and closer to the pivot point of the typical movement of the waveguide conduit distal end 82, controlled by the wrist and fingers. Thus greater precision in controlling the gripping portion and the delivery and application of the laser radiation through a waveguide 84 is achieved and hand and finger fatigue can be reduced.

Figure 5:
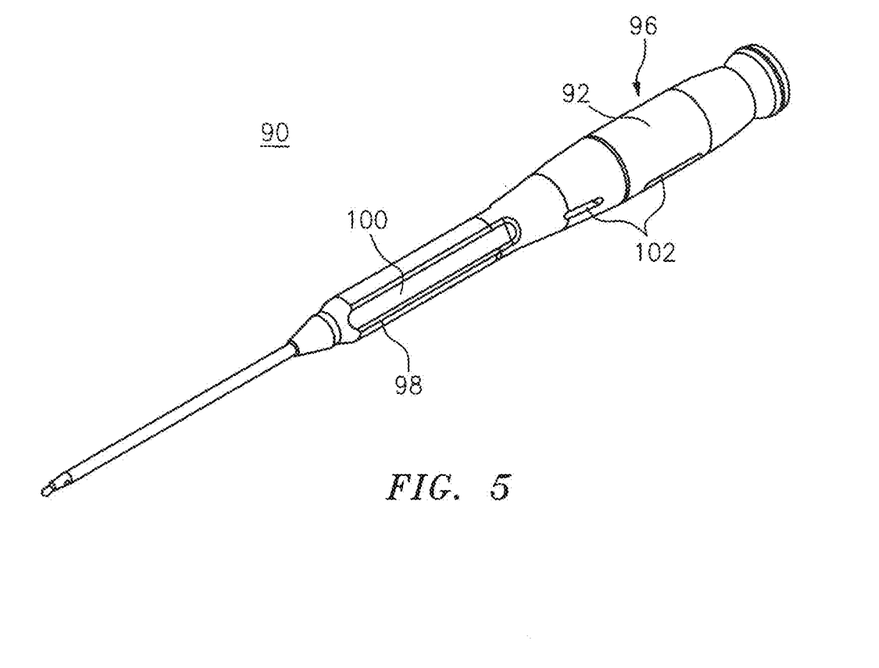
FIG. 5 is a schematic perspective view of a waveguide conduit having a counterbalance portion with a variable cross-section profile, in accordance with an embodiment of the invention.

Laser radiation delivery structure 90, FIG. 5, has a handle portion 91 with a counterbalance portion 92 and a gripping portion 98. Counterbalance portion 92 has a variable, asymmetric cross-sectional profile and preferably has a largest cross-sectional dimension, such as at longitudinal location 96, that is at least as large as the largest cross-sectional dimension of the gripping portion 98 of the handle, preferably larger as illustrated in FIG. 5. This configuration can relieve pressure on the hand and allow better stability. In such embodiments, the shift in the waveguide conduit center of mass is achieved by simply having larger dimensions at the counterbalance portion, compared to the gripping portion, and therefore greater mass. In other words, fabricating counterbalance portion 92 with denser materials is not needed when its diameter is increased. Similarly, gripping portion 98 can have reduced-diameter "flats" or grooves which both reduce weight and enhance gripping by the fingers of a user.

Alternatively or additionally, the mass distribution can be effected by using lighter materials for the gripping portion 98, for example, aluminum and plastics, and heavier materials for the counterbalance portion, for example stainless steel. Alternatively or additionally, fine control of the mass distribution can be achieved by implementing hollow structures in the gripping portion and/or the counterbalance section, such as openings 102 as illustrated in FIG. 5. Such an approach can be useful when cannulas of different lengths are required for the waveguide conduits for different surgical procedures, although the handle portion 91 preferably has the same overall dimensions for all implementations. In such embodiments, waveguide conduits with longer cannulas, requiring more counterbalance, may have the counterbalance without any hollow structures 102, while waveguide conduits with shorter cannulas may have the counterbalance portions that include hollow structures 102. Hollow structures preferably also facilitate cleaning and sterilization of the waveguide conduit by allowing additional fluid access to lumens, cavities and chambers within handle portion 91.

Figures 6A, 6B:
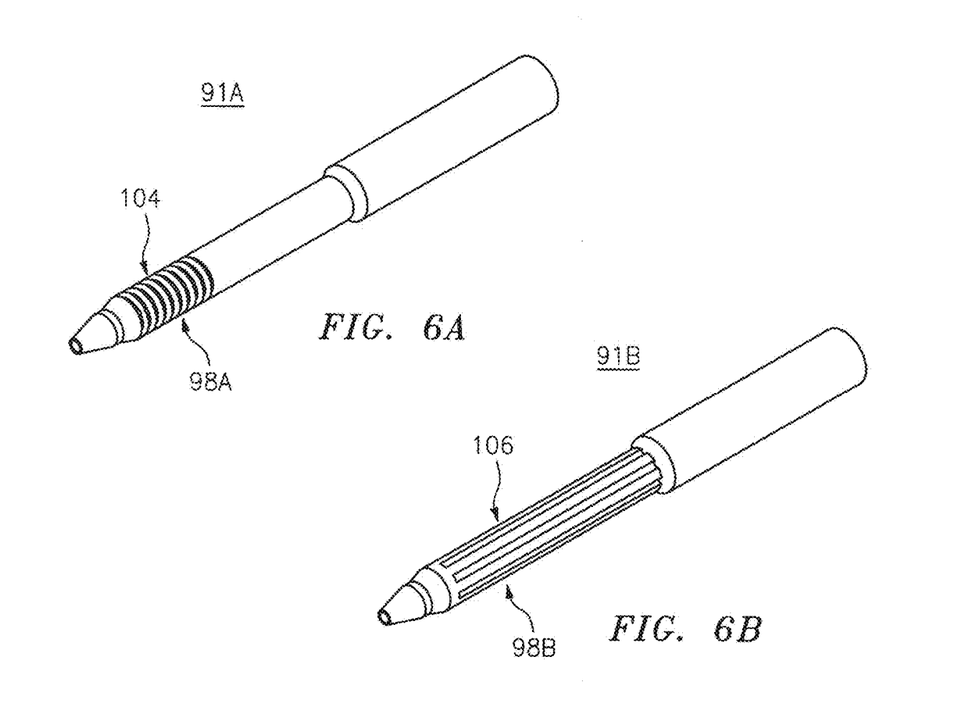
FIGS. 6A and 6B are schematic perspective views of a waveguide conduit having a gripping portion with circumferential and axial ribs, respectively, in accordance with an embodiment of the invention.

In one embodiment of the present invention, as illustrated in FIG. 5, the counterbalance portion 92 is cylindrical and the gripping portion 98 is cylindrical with flats 100 to enhance control of the waveguide conduit manipulation. For example, three flats are spaced equally around the circumference of the gripping portion, and to provide comfort and precise control of the waveguide conduit in the hand grip when the thumb, the index and the middle fingers are used to hold and move the instrument. The flats are especially helpful when subtle, precise rotational movements of the waveguide conduit are to be executed. In general, the exact shapes and sizes of the both the gripping portion and the counterbalance portion may be determined by desired ergonomics of the waveguide conduit for specific surgical uses or surgeon preferences. For example, different types of handle portions with different gripping portions include: (i) a handle portion with a completely cylindrical gripping portion; (ii) a handle portion 91, FIG. 5, with a cylindrical gripping portion 98 with multiple flats 100; (iii) a handle portion 91A, FIG. 6A, having a cylindrical gripping portion 98A with circumferential ribs 104; a handle portion 91B, FIG. 6B, having a cylindrical gripping portion 98B with axial ribs 106; or a combination of some or all these features. Various surface patterns can also be applied to the gripping portion to improve gripping and control of the waveguide conduit manipulation by the surgeon's gripping fingers, for example knurling. Non-cylindrical gripping portion profiles are also contemplated, such as oval, triangular, or other non-circular cross-sectional geometries.

Figure 7:
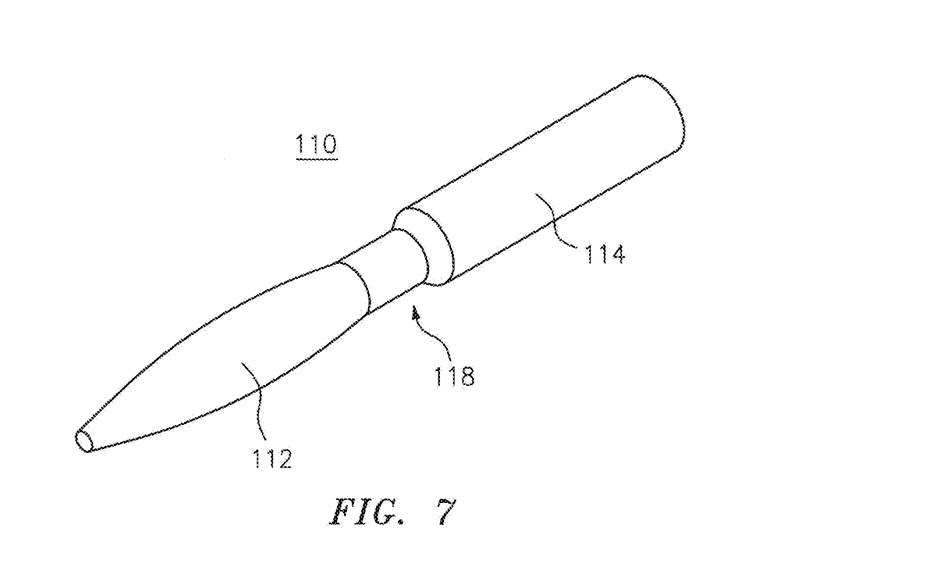
FIG. 7 is a schematic perspective view of a waveguide conduit having (i) a gripping portion with a pen style grip and (ii) a cylindrical counterbalance portion, in accordance with an embodiment of the invention.

In yet another construction, a handle portion 110, FIG. 7 has a gripping portion 112 with a smooth outer surface that is shaped with a varying diameter with an elliptical cross-section along its longitudinal axis for a pen-style grip. A counterbalance portion 114 is shaped as a straight, uniform cylinder in this construction and joins with gripping portion 112 at a narrowed transition region or waist 118.

Figure 8:
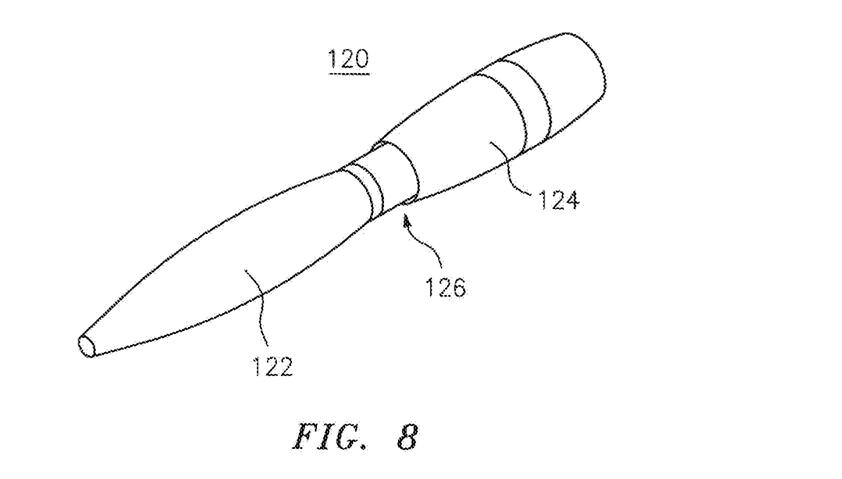
FIG. 8 is a schematic perspective view of a waveguide conduit having (i) a gripping portion with a pen style grip and (ii) a barrel-shaped, asymmetrical counterbalance portion, in accordance with an embodiment of the invention.

Alternatively, a handle portion 120, FIG. 8, has a pen-shaped gripping portion 122, a transition region 126, and a counterbalance portion 124 with an asymmetrical, barrel-like shape. In other constructions, the counterbalance portion has an elliptical cross-section, or has a varying cross-section along its length, such as depicted in FIG. 4.

In general, a gripping portion of a handle portion according to the present invention typically has a cross-sectional diameter of between about 4 mm and about 15 mm and a length between about 20 mm and about 75 mm. The counterbalance portion typically has a cross-sectional diameter between 5 mm and 30 mm and a length between about 20 mm and about 80 mm. The overall length of the handle portion of the waveguide conduit is preferably between about 30 mm and about 155 mm.

Figure 9:
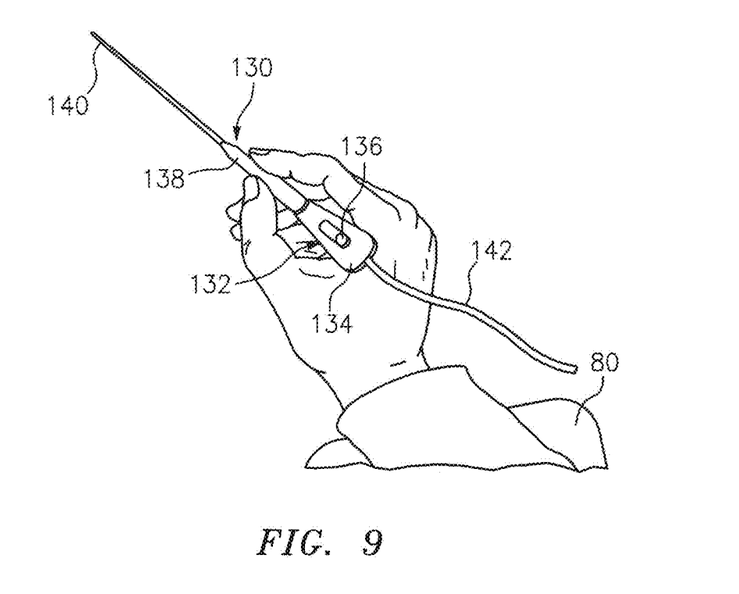
FIG. 9 is a schematic perspective view of a waveguide conduit having a counterbalance portion with a waveguide lock, in accordance with an embodiment of the invention.

Laser radiation delivery structure 130, FIG. 9, has a handle portion 132 with a counterbalance portion 134 including a waveguide lock 136, and a gripping portion 138. Delivery structure 130 further includes a cannula 140 and receives a waveguide 142 therethrough. The waveguide lock 136 includes a slide button lock actuator as illustrated in FIG. 9; in other constructions, another actuator such as a push button mechanism is actuated to release the waveguide.

Waveguide locks according to the present invention have a gripping mechanism that prevents a single-use waveguide disposed in the reusable waveguide conduit from moving axially and preferably rotationally when locked, and a control mechanism that allows a user to insert and lock the waveguide in place and release the waveguide when needed. The gripping mechanism generally provides enough retention force to prevent accidental slippage of the waveguide out of alignment with the distal portion of the waveguide conduit during use. At the same time, the gripping mechanism is gentle enough to not overly squeeze the waveguide and to not cause any mechanical degradation and/or any deleterious effects on the waveguide optical performance, such as increased optical loss due to slight deformation at the pressure point, waveguide micro bending, or even optical breakdown failure. The control mechanism for the waveguide lock preferably is easy for a user to operate and is ergonomically user-friendly, but at the same time prevents accidental release of the waveguide during normal manipulation and handling of the waveguide conduit.

Figure 10:
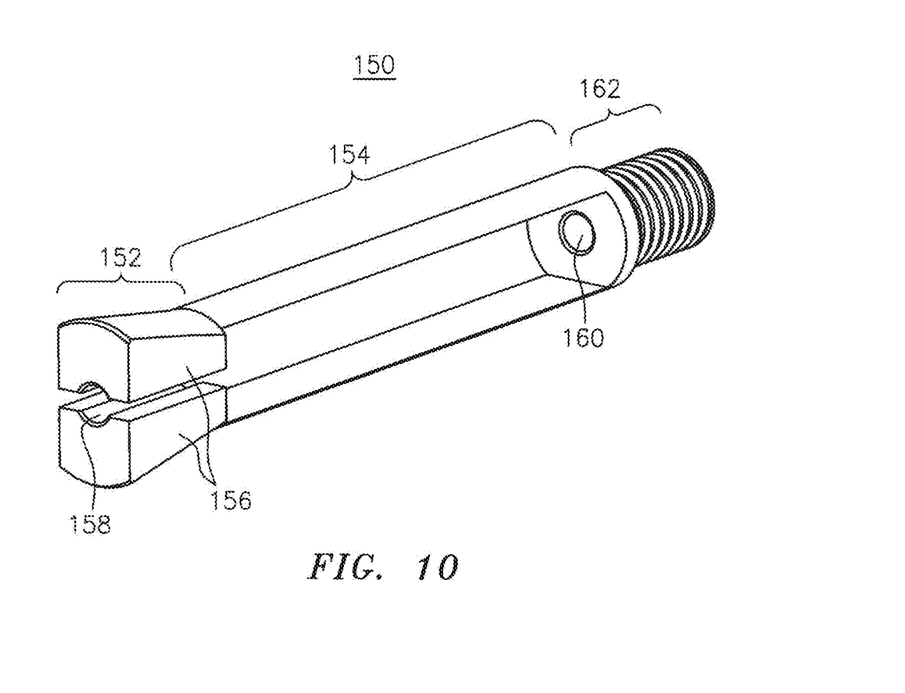
FIG. 10 is a schematic perspective view of a waveguide lock having a collet structure with two jaws and two cantilevered arms, in accordance with an embodiment of the invention.

As described above in relation to FIG. 3, in one construction the waveguide lock includes a spring and a collet structure. Referring more particularly to FIG. 10, a collet structure 150 preferably includes at least two jaws 152 and at least two cantilevered arms 154, each jaw being disposed on a distal end of a cantilevered arm 154. Each jaw 152 has an arcuate outer profile with flat side cuts and a taper or chamfer 156 with a decreasing, ever-smaller diameter or thickness progressing proximally toward arms 154, which drives the jaws to close when the jaws are biased into a surrounding conical formation of smaller internal diameter than the diameter of the jaws. The jaws define a cylindrical opening 158 in the center for gripping the waveguide, which is smaller than the cylindrical opening 160 through threaded interconnect 162.

Figure 11:
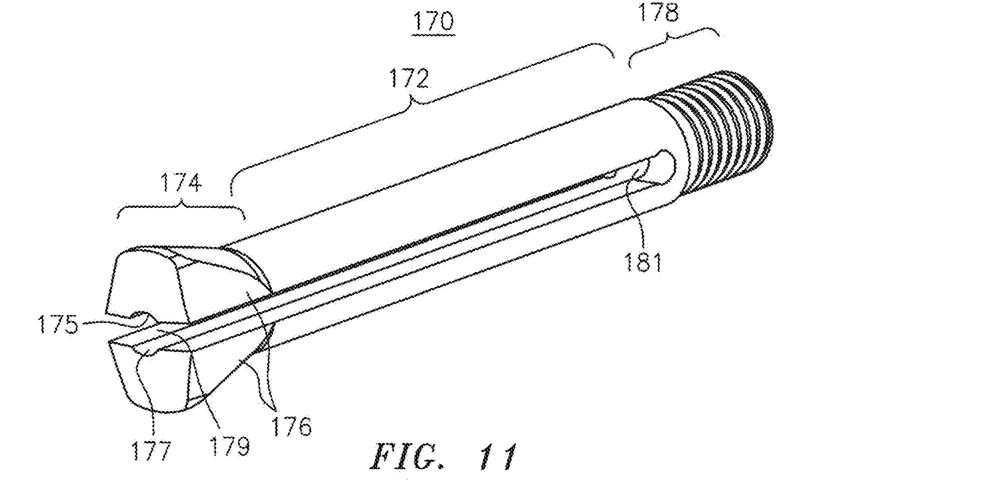
FIG. 11 is a schematic perspective view of the jaws and cantilever arms of a collet structure of a waveguide lock, in accordance with an embodiment of the invention.

Cantilevered arms in locking mechanisms utilized according to the present invention may have certain geometrical dimensions defining particular flexure properties to allow the jaws to open and close. For example, a collet structure 170, FIG. 11, has thicker cantilevered arms 172 which may be useful when the collet structure is made of less rigid materials such as certain polymeric materials. Jaws 174 define steeper-tapered chamfers 176 on their outer surfaces. Grooves 175 and 177 extend along an entire length of the cantilevered arms 172, from distal opening 179 between jaws 174 and circular opening 181 in interconnect 178 to which the cantilevered arms 172 are attached. The interconnect section 178 has a cylindrical opening 181 to allow a waveguide to pass freely therethrough. The interconnect section 178 has a threaded end utilized to attach the collet structure 170 to other elements of the waveguide lock, for example a release push button, simplifying the assembly of the waveguide lock during manufacturing.

Figure 12:
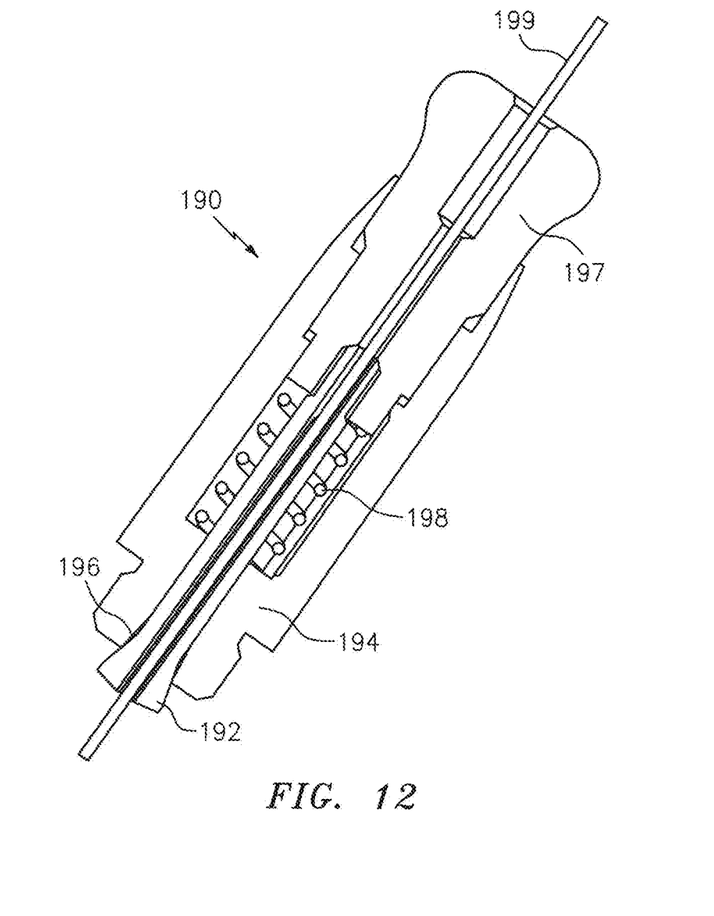
FIG. 12 is a schematic cross-sectional view of a waveguide lock assembly with a collet structure engaging a single-use waveguide, in accordance with an embodiment of the invention.
Figure 13:
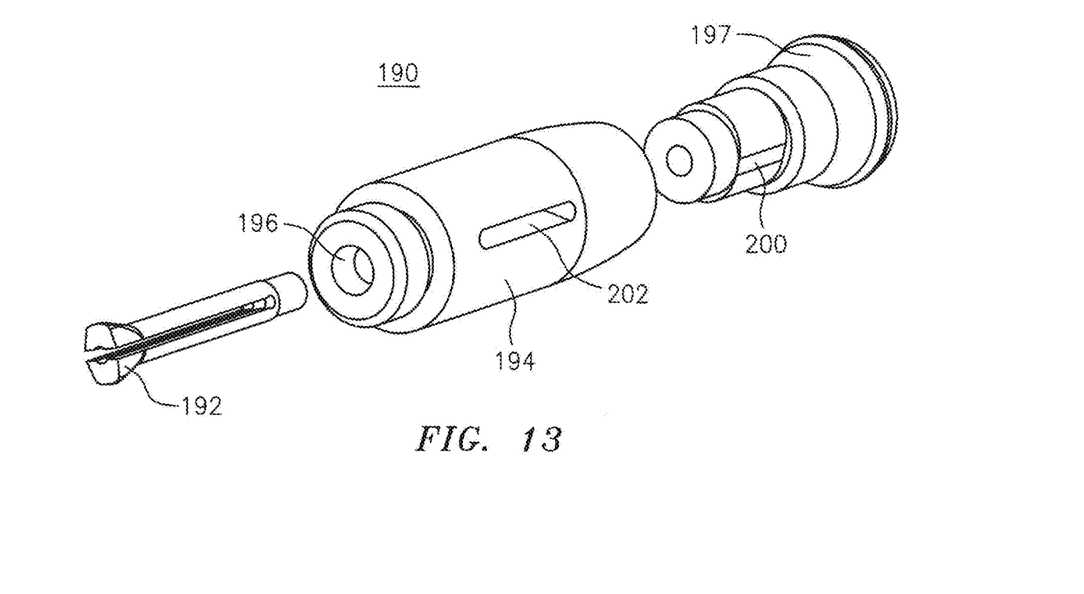
FIG. 13 is a schematic perspective view of the construction details of the waveguide lock assembly of FIG. 12.

A waveguide lock assembly 190, FIGS. 12 and 13, includes a collet structure 192 slidably disposed within a waveguide lock housing 194, preferably defined by a handle portion, such as in a counterbalance portion according to an aspect of the present invention. The housing 194 has a conical taper 196 to constrict the jaws of the collet structure 192. The collet structure preferably is be spring-loaded, that is, biased closed by spring 198, FIG. 12, so that when the waveguide lock is in a locked state, the jaws are located inside the conical formation and thus automatically clamp onto a waveguide 199. The collet structure 192 is directly attached by the collet structure interconnect to a release push button 197 in this construction. An inner-disposed compression spring 198 is preloaded to keep the collet structure jaws closed, thus keeping the waveguide lock in the locked state. Pushing on the release button 197 compresses the spring 198 further and moves the collet structure jaws out of the waveguide lock housing conical taper 196, thus opening the collet structure jaws and transitioning the waveguide lock into an open state. The waveguide open state with collet structure jaws open is maintained only as long as the release button 197 is manually depressed. In the embodiment illustrated in FIG. 12, the release push button 197 has a circular cross-section. Actuation and spring force are substantially aligned or parallel with the longitudinal axis of the waveguide.

An expanded assembly view of waveguide lock assembly 190 is illustrated in FIG. 13, with the push button 197 having a section with flats 200 and a corresponding section containing mating flat sides inside the waveguide lock housing, to prevent rotation of the release push button and the collet structure inside the waveguide lock housing. Alternatively, the push button may have an elliptical cross-section region and corresponding elliptical section inside the waveguide lock housing. In other embodiments, the push button can be elliptical over its entire shape, or square with rounded edges, or otherwise shaped with a corresponding mating shape of the waveguide housing. In embodiments where the waveguide lock is located in the counterbalance portion of other than a round shape, a non-round release push button may be advantageous.

The waveguide lock housing 194 preferably includes openings 202 for cleaning and sterilization. These openings 202 may also be utilized to control mass distribution in the embodiments with finely tuned counterbalance portions including the waveguide lock.

The spring loaded collet structure allows more precise control of both the compression force exerted on the waveguide and the retention force during use, because both are determined by the collet structure geometry and the force of the loaded spring and have little dependence on waveguide diameter. The gripping performance of the spring-loaded collet structure is also preferably independent of user action, because the user action is limited to releasing the waveguide, while waveguide gripping action is automatic due to the pre-loaded spring. Moreover, upon application of tensile retraction force on the locked waveguide in the direction of waveguide withdrawal from the waveguide conduit, the friction may cause the collet structure jaws to compress more by virtue of the jaw chambers and the waveguide lock housing conical taper, thus ensuring retention of the waveguide in place. At the same time, the collet structure jaws may allow close surface contact with the waveguide outside diameter for gripping action, with relatively even distribution of compression force on the waveguide along the waveguide circumference, in comparison to, e.g., a flat clamp type mechanism, thus allowing much less stress on the waveguide and resulting in negligible effect on the waveguide optical performance and reliability.

The waveguide lock may be used to retain a waveguide with a predetermined retention force, determined by the spring force and the collet structure materials and geometry. The waveguide lock release button actuation force may be determined by the spring force. In a preferred embodiment, the spring force may be selected to provide required resistance to the release button and ensure adequate bias into locked state of the waveguide lock. The release force may be in the range from 0.5 lb to 2.5 lb. Springs with rates 2 lb/in to 10 lb/in with compression by 0.1 in to 0.5 in may be used to achieve the required release force. Given the spring force, the collet geometry is preferably designed to provide adequate gripping action. The collet structure jaw chamfers may have angles from 5 degrees to 60 degrees. In a preferred embodiment, the chamfer angle is 15 degrees. The length of the jaws determines the pressure on the waveguide when locked, given the jaws compression force. For more delicate waveguides, the jaws may be longer to increase surface contact and reduce pressure. For more mechanically rugged waveguides the jaws may be relatively short. For example, the jaws' length can be selected from the range of 0.5 mm to 20 mm. In a preferred embodiment the jaws' length is 3 mm.

Additional design considerations of the collet structure geometry and the spring may be required for the described mechanism to operate over a wide range of waveguide diameters while providing consistent compression on the waveguide and retention force. FIG. 10 depicts the certain design elements of the collet structure. For example, a length of the cantilevered arms may be about 2 to 5 times the length of the collet structure jaws or even longer. A length of the jaws is at least the waveguide diameter, or longer, for example from about 2 times the waveguide diameter to about 10 times the waveguide diameter. The diameter of a cylindrical opening in the collet structure through which the waveguide may pass is preferably close to the largest waveguide diameter or larger. For example, the diameter may be 0.05 mm larger, or 0.1 mm larger, or 0.15 mm larger, or by 5% to 20% larger. It is understandable that the cylindrical opening in the jaws of the collet structure may be close to the waveguide diameter to ensure maximum gripping action while maintaining minimal pressure on the waveguide, but the opening between the cantilever arms and the opening in the collet structure interconnect may be substantially larger, as large as 1.5 time to 10 times the waveguide diameter.

Other embodiments of the collet structure include circumferential ridges or helical threads on the jaw ID to improve axial grip. Axial ridges may be added, alone or in combination, to minimize rotational movement of the waveguide. The opening in the collet structure for the waveguide can be of cylindrical cross-section or another shape, for example, square or rhomb cross-section. Also, there may be three or more arms and jaws. Alternatively, a single arm and jaw can be used to bias and clamp the waveguide against an interior portion of the housing.

Figure 14:
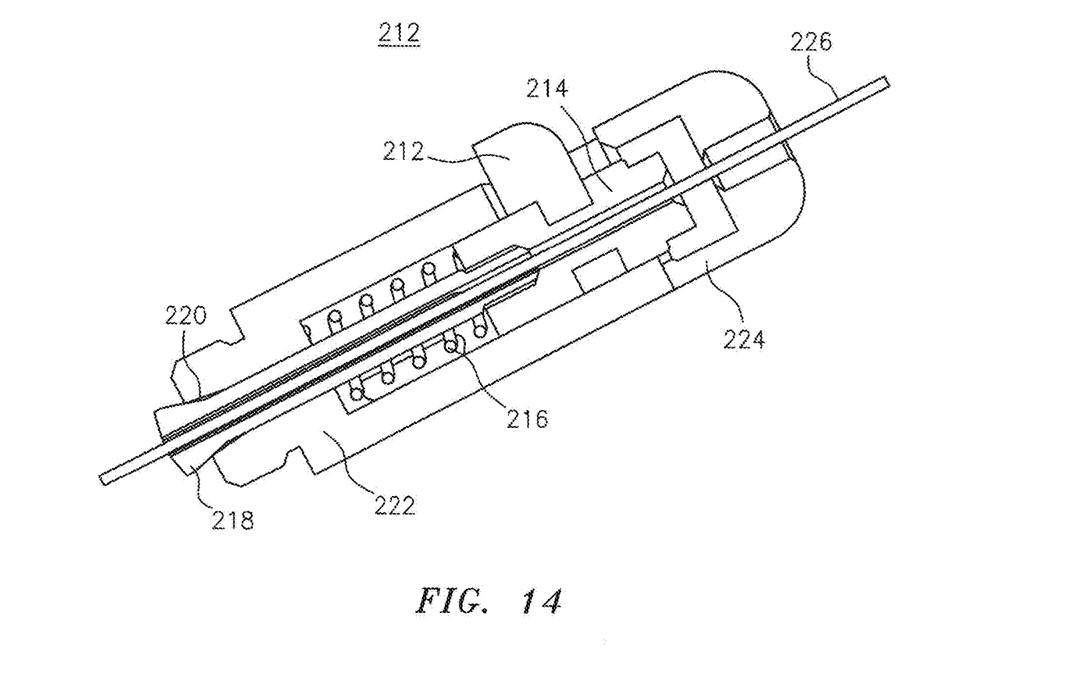
FIG. 14 is a schematic perspective view a waveguide lock assembly including a slide button, in accordance with an embodiment of the invention.

The control mechanism in this embodiment may be a release button, such as a push button, which compresses the spring and thus allows the jaws of the collet structure to expand and release the waveguide. Alternatively, the release button may be a slide button. An embodiment of a waveguide lock assembly 210 with a release slide button 212 is shown in FIG. 14 engaging a waveguide 226. Release slide button 212 is coupled to the collet structure actuator 214 which in turn couples with the spring 216 and the collet structure 218 and transmits the release button action to the spring 216 and the collet structure 218 to change the waveguide lock state from closed to open by moving the jaws of collet structure 218 away from conical taper 220 of waveguide lock housing 222. A housing back end cap 224 is attached, preferably fixedly, to the proximal end of housing 222 in this construction. Optionally, the spring 216 may be used in tension, to pull the collet 218 into the locked state, or the spring 216 may be placed to react directly against the jaws of collet 218.

Yet another waveguide lock assembly 230 according to the present invention is illustrated in a locked state in FIGS. 15-18B. In one detailed construction as shown, components of assembly 230 include a push button 232, a movable lock element 234, a fixed lock body 236 that defines a bridge 241 and a cavity 243, a rear spring 240, a front spring 242, a rear dowel pin 244, a front dowel pin 246, set screws 250 and 252 which fix lock body 236 within a handpiece by engaging passages 251 and 253, FIG. 18B, and a longitudinal lumen 248, FIGS. 15 and 18A, through which a single-use waveguide is passed when push button 232 is forcibly depressed to overcome the upward biasing force of springs 240, 242.

Figure 16:
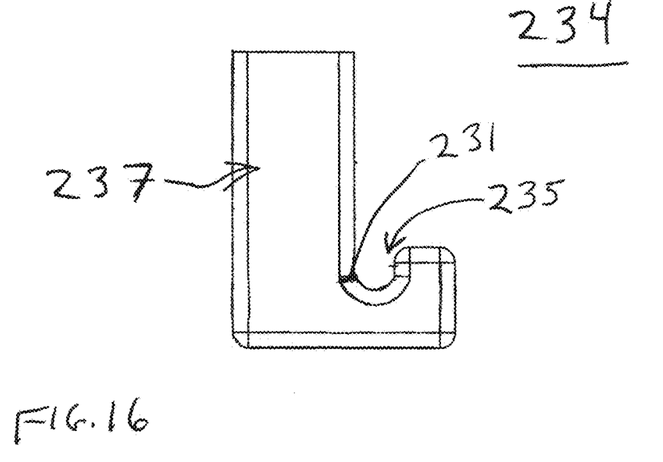
FIG. 16 is a schematic side view of the movable waveguide lock element of FIG. 15.
Figure 17:
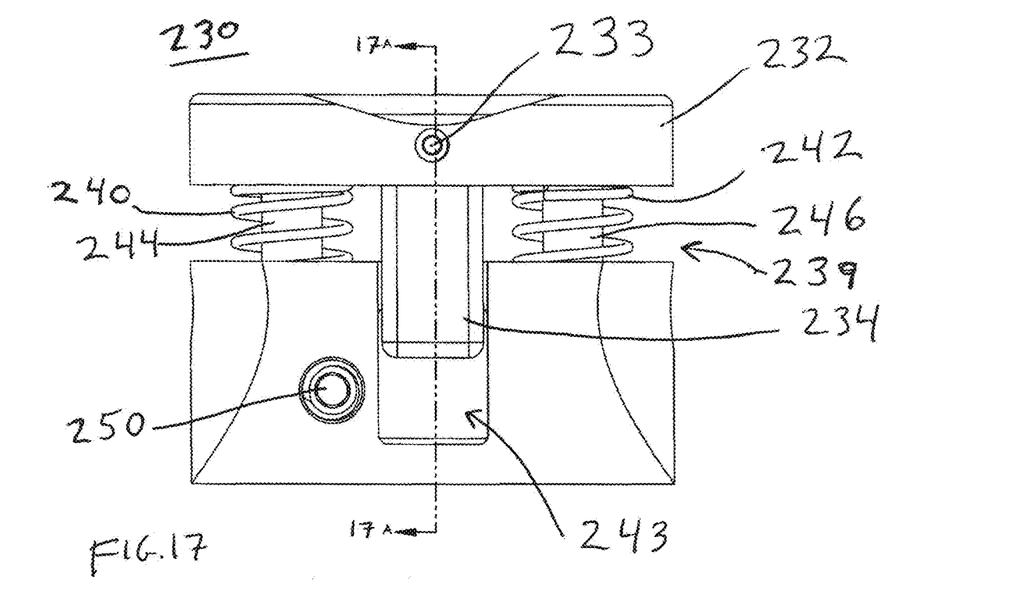
FIG. 17 is a schematic side view of the assembly of FIG. 15.
Figure 17A:
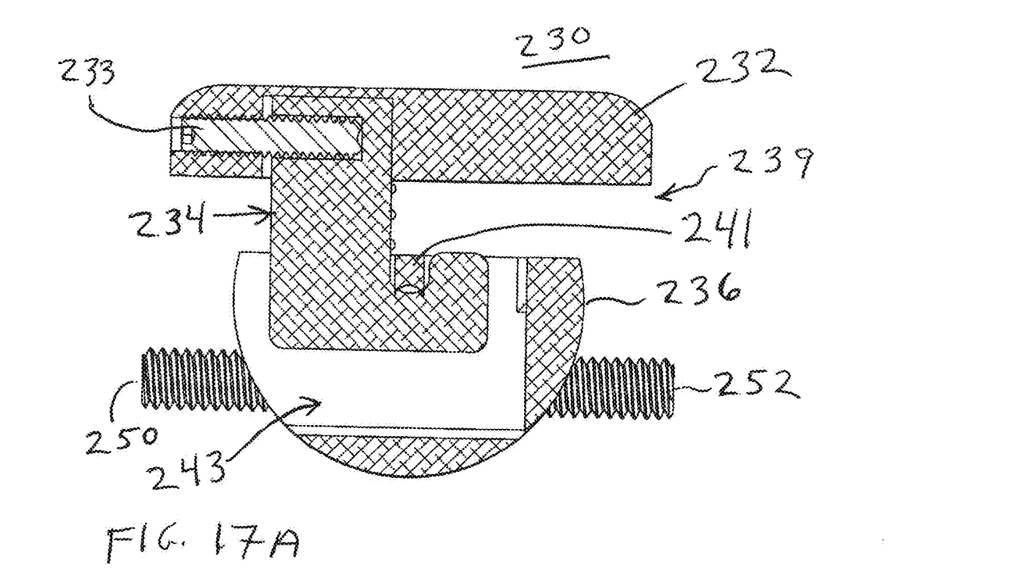
FIG. 17A is a schematic cross-sectional view along lines 17A-17A of FIG. 17.
Figure 18A:
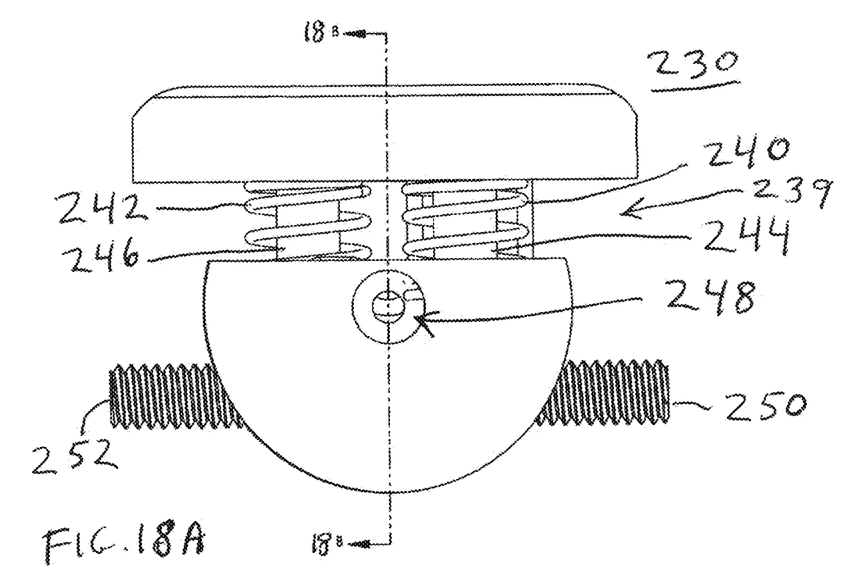
FIG. 18A is a schematic rear view of the assembly of FIG. 15.
Figure 18B:
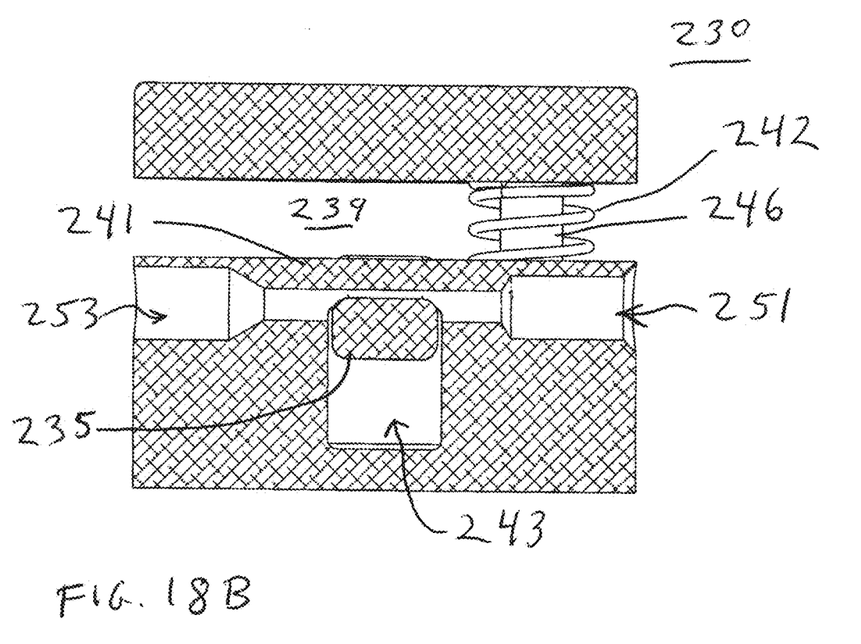
FIG. 18B is a schematic cross-sectional view along lines 18B-18B of FIG. 18A.

When the underside of button 232 contacts stop surface 238 of lock body 236, and closes gap 239 normally established between them in the locked state, then clamp surface 235, best shown in FIGS. 16, 17A and 18B, is driven away from bridge 241 of body 236 to open a gap between clamp surface 235 and bridge 241 that, preferably, is at least as great in free-space diameter as the diameter of lumen 248 to enable slidable translation of the waveguide relative to body 236. Lock element 234 travels within a cavity 243 formed within lock body 236.

As best illustrated in FIGS. 16 and 17A, it is preferable for clamp surface 235 and the underside of bridge 241 to be concave along the longitudinal axis of lock assembly 230 to better conform to a cylindrical waveguide passed therethrough. As shown in FIG. 16, the edges of lock element 234 preferably are chamfered, such as with chamfer 231. An upper leg 237 of lock element 234 is fixed to button 232 by a set screw 233, FIGS. 15, 17 and 17A.

Figure 15:
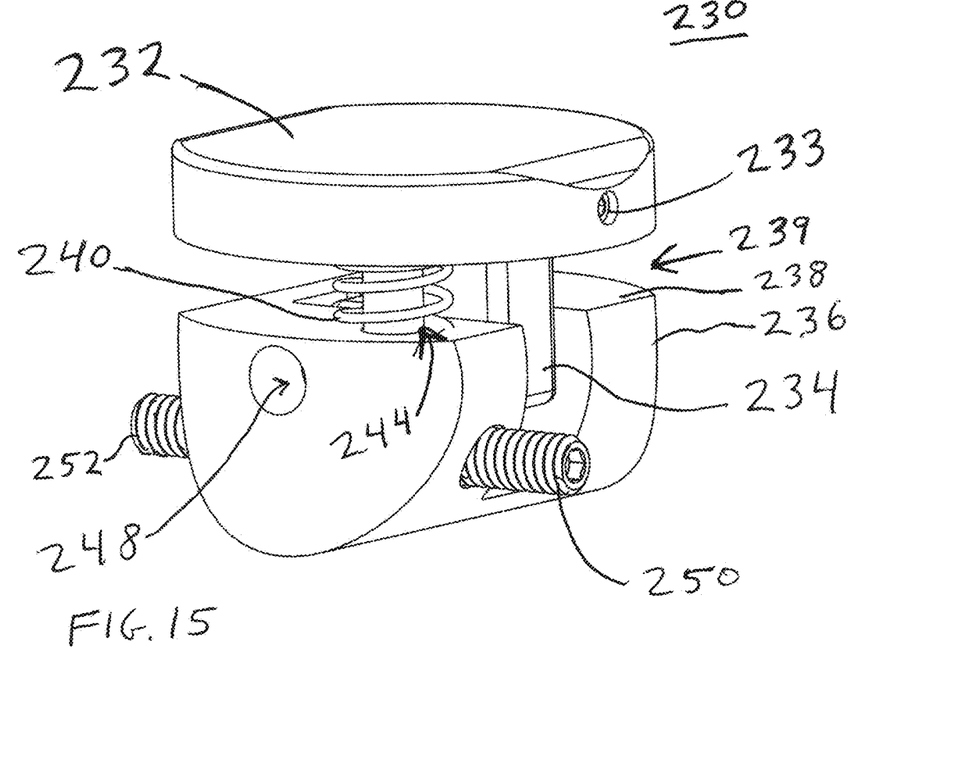
FIG. 15 is a schematic perspective view of an alternative waveguide lock assembly having push-button-actuated release of a movable waveguide lock element.

Dowel pins 244, 246 serve as guides to control the radial movement of button 232 and are fixed in lock body 236 in one construction and, in another construction, move in conjunction with button 232 and lock element 236 when actuated by a user. When placed in a handle portion of a handpiece during manufacture or assembly, button 232 is raised above the outer surface of the handle portion in one construction, is flush with the outer surface in a second construction, and is recessed relative to the outer surface in a third construction. The lock assembly 230 may be less prone to inadvertent actuation in the flush and recessed constructions.

Although specific features of the present invention are shown in some drawings and not in others, this is for convenience only, as each feature may be combined with any or all of the other features in accordance with the invention. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A device, comprising:
   a handle housing having a distal end and a proximal end, an inner surface of the handle housing defining a first portion of a waveguide conduit;
   a waveguide lock housing having a distal end and a proximal end, the distal end of the waveguide lock housing operably secured to the proximal end of the handle housing;
   a collet positioned at least partially within the waveguide lock housing;
   a push button positioned at least partially within the waveguide lock housing and connected to the collet, inner surfaces of the push button and the collet defining a second portion of the waveguide conduit; and
   a spring positioned within the waveguide lock housing that biases the push button and the collet in a proximal direction relative to the distal end of the waveguide lock housing.

2. The device of claim 1 wherein the collet includes at least two jaws and at least two cantilevered arms, each jaw being disposed on a distal end of a respective one of the cantilevered arms.

3. The device of claim 1 wherein the device has a center of mass located closer to a proximal end of the device than to a distal end of the device.

4. The device of claim 3 wherein the center of mass is located between the distal end and the proximal end of the waveguide lock housing.

5. The device of claim 1 wherein the first portion of the waveguide conduit and the second portion of the waveguide conduit are aligned with one another along an axis extending through the distal end of the handle housing and a proximal end of the push button.

6. The device of claim 1 wherein the waveguide lock housing has a first inner surface, the collet has a first outer surface slidably engaged with the first inner surface of the waveguide lock housing, and at least one of the first inner surface of the waveguide lock housing and the first outer surface of the collet is tapered.

7. The device of claim 1, further comprising a waveguide positioned within the first portion and the second portion of the waveguide conduit.

8. The device of claim 1 wherein the handle housing defines a chamber, a distal end of the collet positioned at least partially within the chamber, the distal end of the collet advanceable distally into the chamber in response to the push button being depressed toward the handle housing.

9. The device of claim 1, further comprising a cannula physically coupled to the handle housing, the cannula defining a third portion of the waveguide conduit.

10. The device of claim 1 wherein the collet is threadably connected to the push button.

11. The device of claim 1 wherein the waveguide lock housing includes at least one opening for cleaning and sterilization.

12. A method, comprising:
   selecting a laser radiation delivery device including a surgical access portion, a handle portion and a waveguide conduit that extends through the surgical access portion and the handle portion, the handle portion having a gripping portion and a waveguide lock, wherein the waveguide lock is operable in a locked state and an unlocked state;
   pressing a spring-biased push button positioned at a proximal end of the handle portion in a distal direction to place the waveguide lock in the unlocked state;
   inserting a waveguide into the waveguide conduit while the waveguide lock is in the unlocked state; and
   releasing the push button to place the waveguide lock in the locked state in which the waveguide lock fixedly holds the waveguide in a selected axial position relative to the waveguide conduit.

13. The method of claim 12 wherein placing the waveguide lock in the locked state includes allowing the waveguide lock to return to the locked state.

14. The method of claim 12 wherein inserting the waveguide into the waveguide conduit includes inserting the waveguide into the waveguide conduit through an opening at a proximal end of the spring-biased push button.

15. A method, comprising:
   positioning a collet at least partially within a waveguide lock housing having a distal end and a proximal end, a portion of the collet extending through the distal end of the waveguide lock housing;
   positioning a spring within the waveguide lock housing between the distal end and the proximal end of the waveguide lock housing;
   positioning a push button at least partially within the waveguide lock housing, the spring being between the push button and the distal end of the waveguide lock housing;
   physically coupling the push button to the collet, the spring biases the push button and the collet in a proximal direction relative to the distal end of the waveguide lock housing; and
   physically coupling the distal end of the waveguide lock housing to a proximal end of a handle housing,
   wherein an inner surface of the handle housing defines a first portion of a waveguide conduit, and inner surfaces of the push button and the collet define a second portion of the waveguide conduit.

16. The method of claim 15 wherein physically coupling the distal end of the waveguide lock housing to the proximal end of the handle housing includes aligning the first and the second portions of the waveguide with one another along an axis extending through a distal end of the handle housing and a proximal end of the push button.

17. The method of claim 15 wherein physically coupling the push button to the collet includes physically coupling the push button to a threaded end of the collet.

18. The method of claim 15 wherein physically coupling the distal end of the waveguide lock housing to the proximal end of the handle housing includes positioning the portion of the collet extending through the distal end of the waveguide lock housing within a chamber in the handle housing.

19. The method of claim 18, further comprising:
advancing the portion of the collet distally into the chamber, from a locked position to an unlocked position, by depressing the push button;
inserting a waveguide through the second portion of the waveguide conduit and into the first portion of the waveguide conduit while the collet is in the unlocked position; and
fixing a position of the waveguide by releasing the push button and retracting the portion of the collet proximally into the locked position.

* * * * *